US00PP20004P2

(12) United States Plant Patent
van Rysselberghe

(10) Patent No.: US PP20,004 P2
(45) Date of Patent: May 19, 2009

(54) GLOXINIA PLANT NAMED 'SONATA VIOLET 1'

(50) Latin Name: *Sinningia speciosa*
Varietal Denomination: Sonata Violet 1

(75) Inventor: Ronie van Rysselberghe, Lochristi (BE)

(73) Assignee: MicroFlor NV, Lochristi (BE)

( * ) Notice: Subject to any disclaimer, the term of this patent is extended or adjusted under 35 U.S.C. 154(b) by 0 days.

(21) Appl. No.: 12/012,913

(22) Filed: Feb. 6, 2008

Related U.S. Application Data

(60) Provisional application No. 60/872,433, filed on Jun. 26, 2007.

(51) Int. Cl.
*A01H 5/00* (2006.01)

(52) U.S. Cl. ..... Plt./482

(58) Field of Classification Search ..... Plt./482, Plt./263
See application file for complete search history.

(56) References Cited

PUBLICATIONS

UPOV–ROM GTITM, Plant Variety Database, 2008/01, GTI Jouve Retrieval Software, citation for 'Sonata Violet 1'.*

* cited by examiner

*Primary Examiner*—S. B. McCormick Ewoldt

(57) ABSTRACT

A new cultivar of Gloxinia plant named 'Sonata Violet 1' that is characterized by large green leaves and flowers that are purple-violet toward the center and violet toward the outside.

1 Drawing Sheet

Botanical classification: *Sinningia speciosa.*
Variety denomination: 'Sonata Violet 1'.

BACKGROUND OF THE INVENTION

The present invention relates to a new and distinct cultivar of Gloxinia plant botanically known as *Sinningia speciosa* and hereinafter referred to by the cultivar name 'Sonata Violet 1'.

The new cultivar is the product of a breeding program conducted by the inventor in a cultivated area of Lochristi, Belgium.

'Sonata Violet 1' is a hybrid that originated from the hybridization of the female or seed parent a proprietary *Sinningia speciosa* cultivar named 'A' (not patented) and the male or pollen parent a proprietary *Sinningia speciosa* cultivar named 'DSB004' (not patented). The cultivar 'Sonata Violet 1' was selected by the inventor in 2003 as a single plant within the progeny of the stated cross in Lochristi, Belgium.

Asexual reproduction of the new cultivar 'Sonata Violet 1' first occurred by tissue culture in 2003 in Lochristi, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Gloxinia cultivar 'Sonata Violet 1'. These traits in combination distinguish 'Sonata Violet 1' as a new and distinct cultivar apart from other existing known varieties of Gloxinia.

1. Gloxinia 'Sonata Violet 1' exhibits large green leaves.

2. Gloxinia 'Sonata Violet 1' exhibits flowers that are purple-violet toward the center and violet toward the outside.

The closest comparison cultivar is Gloxinia 'Amoroso Violet' (not patented). 'Sonata Violet 1' is distinguishable from 'Amoroso Violet' by the following characteristics:

1. 'Sonata Violet 1' exhibits smaller flowers.
2. 'Sonata Violet 1' exhibits a smaller overall size.

The new cultivar 'Sonata Violet 1' is distinguishable from the female parent 'A' by the following characteristics:

1. 'Sonata Violet 1' exhibits double flowers.

The new cultivar 'Sonata Violet 1' is distinguishable from the male parent 'DSB004' by the following characteristics:

1. 'Sonata Violet 1' exhibits larger leaves.

BRIEF DESCRIPTION OF THE DRAWING

The accompanying photograph illustrates the distinguishing traits of Gloxinia 'Sonata Violet 1'. The plant in the photograph shows an overall view of a 16 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Gloxinia cultivar named 'Sonata Violet 1'. Data was collected in Lochristi, Belgium from 16 week old glass greenhouse grown plants in 11 cm. diameter containers. The time of year was Fall and the temperature range was 20–22 degrees Centigrade during the day and 20–22 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Sonata Violet 1' has not been tested under all possible conditions and phenotypic differences may be observed with variations in environmental, climatic, and cultural conditions, however, without any variance in genotype.

Botanical classification: *Sinningia speciosa* 'Sonata Violet 1'.
Use: Ornamental Annual.
Parentage: 'Sonata Violet 1' is a hybrid plant that resulted from the hybridization of the following parent plants:
*Female parent.*—*Sinningia speciosa* cultivar named 'A'.
*Male parent.*—*Sinningia speciosa* cultivar named 'DSB004'.
Vigor: Low.
Growth habit: Broad flowers in globose inflorescences.
Plant shape: Basal rosette with globose inflorescences in the center.
Suitable container size: 10 cm. pots.
Height: 16.7 cm. in height.
Width: 34.8 cm. in width.
Low temperature tolerance: USDA Zone 10.
High temperature tolerance: 40° Centigrade.
Propagation: Terminal cuttings.
Time to initiate roots: 7 days to initiate roots at 20–22° Centigrade.
Time to produce a rooted cutting or liner: 28–35 days at 20–22° Centigrade.
Crop time: 16 weeks are required to produce a finished flowering plant.
Growth rate: Approximately 5 cm. per month in spring.
Root system: Fine and fibrous.
Stem: Branching habit: No lateral branches; only basal leaves. Pinching: Not required.
Foliage:
*Texture.*—Slightly glossy and rugose.
*Leaf arrangement.*—Basal rosette.
*Compound or single.*—Single.
*Quantity of leaves.*—16.
*Leaf shape.*—Ovate to broad ovate.
*Leaf apex.*—Broad abruptly acute.
*Leaf base.*—Cordate.
*Leaf length.*—12.3 cm. in length.
*Leaf width.*—10.1 cm. in width.
*Pubescence.*—Both sides covered with short hirstute hairs, 0.2 mm, colored white to green-white.
*Leaf margin.*—Crenate.
*Young leaf color* (*lower surface*).—194A to 194B.
*Young leaf color* (*upper surface*).—139A.
*Mature leaf color* (*lower surface*).—194A to 194B.
*Mature leaf color* (*upper surface*).—139A.
*Vein color* (*under surface*).—194B.
*Vein color* (*upper surface*).—144A.
*Venation pattern.*—Pinnate.
*Leaf attachment.*—Petiolate.
*Petiole dimensions.*—3.9 cm. in length, and 6.5 mm. in width.
*Petiole color.*—144A to 144B.
Flower:
*Inflorescence arrangement.*—Solitary flowers cluster in the center of the basal rosette.
*Flowering habit.*—Continuous.
*Quantity of flowers and buds per plant.*—42.
*Natural flowering season.*—Autumn and winter.
*Fragrance.*—None.
*Flower bud length.*—1.1 cm. in length.
*Flower bud diameter.*—8 mm. in diameter.
*Flower bud shape.*—Broad obovate to globose.
*Bud color.*—145A.
*Flower aspect.*—Upright to slightly outward.
*Flower shape.*—Funnelform.
*Flower dimensions.*—6.1 cm. in diameter and 3.6 cm. in height.
*Flower longevity.*—Approximately 7 days.
*Petal appearance.*—Glossy, velvety.
*Petal texture.*—Smooth and velvety.
*Number of petals.*—10.
*Fused or unfused.*—Only the lower 40% are fused.
*Petal shape.*—Spathulate.
*Petal margin.*—Entire, lower 40% fused.
*Petal apex.*—Rounded.
*Petal length.*—3.2 cm. in length.
*Petal width.*—2.6 cm.
*Petal color when opening* (*upper side*).—N79, tips N88A; base 159C with dots 71A to 71B.
*Petal color when opening* (*under side*).—N88B to N88C, base 161B.
*Petal color fully opened* (*upper side*).—N79, tips N88A; base 159C with dots 71A to 71B.
*Petal color fully opened* (*under side*).—N88B to N88C, base 161B.
*Petal color fading to.*—N186A to N186B.
*Self-cleaning or persistent.*—Persistent.
Petaloids:
*Petaloid appearance.*—Smooth, velvety.
*Petaloid arrangement.*—Rotate, funnelform.
*Number of petaloids.*—Average 11.
*Petaloid shape.*—Spathulate, lower 40% fused.
*Petaloid margin.*—Entire, lower 40% fused.
*Petaloid length.*—Average 2.1 cm.
*Petaloid width.*—Average 2.1 cm.
*Young petaloid color.*—N79, tips N88A; base 159C with dots 71A to 71B.
*Mature petaloid color.*—N79, tips N88A; base 159C with dots 71A to 71B.
Sepals:
*Number of sepals.*—Average 7.
*Sepal aspect.*—Rotate.
*Sepal shape.*—Ovate.
*Sepal margin.*—Entire.
*Sepal apex.*—Acute.
*Sepal base.*—Fused cuneate.
*Sepal surface.*—Glossy and pubescent, hairs 0.2 mm.
*Sepal dimensions.*—2.6 cm. in length and 1.0 cm. in width.
*Young sepal color* (*upper side*).—143A to 143B.
*Young sepal color* (*under side*).—143B.
*Mature sepal color* (*upper side*).—143A to 143B.
*Mature sepal color* (*under side*).—143B.
Calyx:
*Calyx shape.*—Rotate.
*Calyx dimensions.*—1.2 cm. in length and 4.9 cm. in diameter.
Peduncle:
*Peduncle dimensions.*—7.6 cm. in length and 6.5 mm. in diameter.
*Peduncle angle.*—10°.
*Peduncle color.*—144A to 144B.
*Peduncle strength.*—Moderately strong.

Reproduction organs:

*Stamen number.*—Average 10.

*Anther shape.*—Strongly deformed, narrow spathulate.

*Anther size.*—Average 3 mm.

*Anther color.*—198A to 198B.

*Amount of pollen.*—Low.

*Pollen color.*—198A to 198B.

*Pistil number.*—Average 5.

*Pistil length.*—Average 1.6 cm. in length.

*Stigma shape.*—Club-shaped.

*Stigma color.*—N187D.

*Style length.*—1.4 cm.

*Style color.*—155D.

*Ovary color.*—155D.

Disease and pest resistance: Plants of the new cultivar have not been observed for disease and pest resistance.

It is claimed:

1. A new and distinct variety of Gloxinia plant named 'Sonata Violet 1' as described and illustrated.

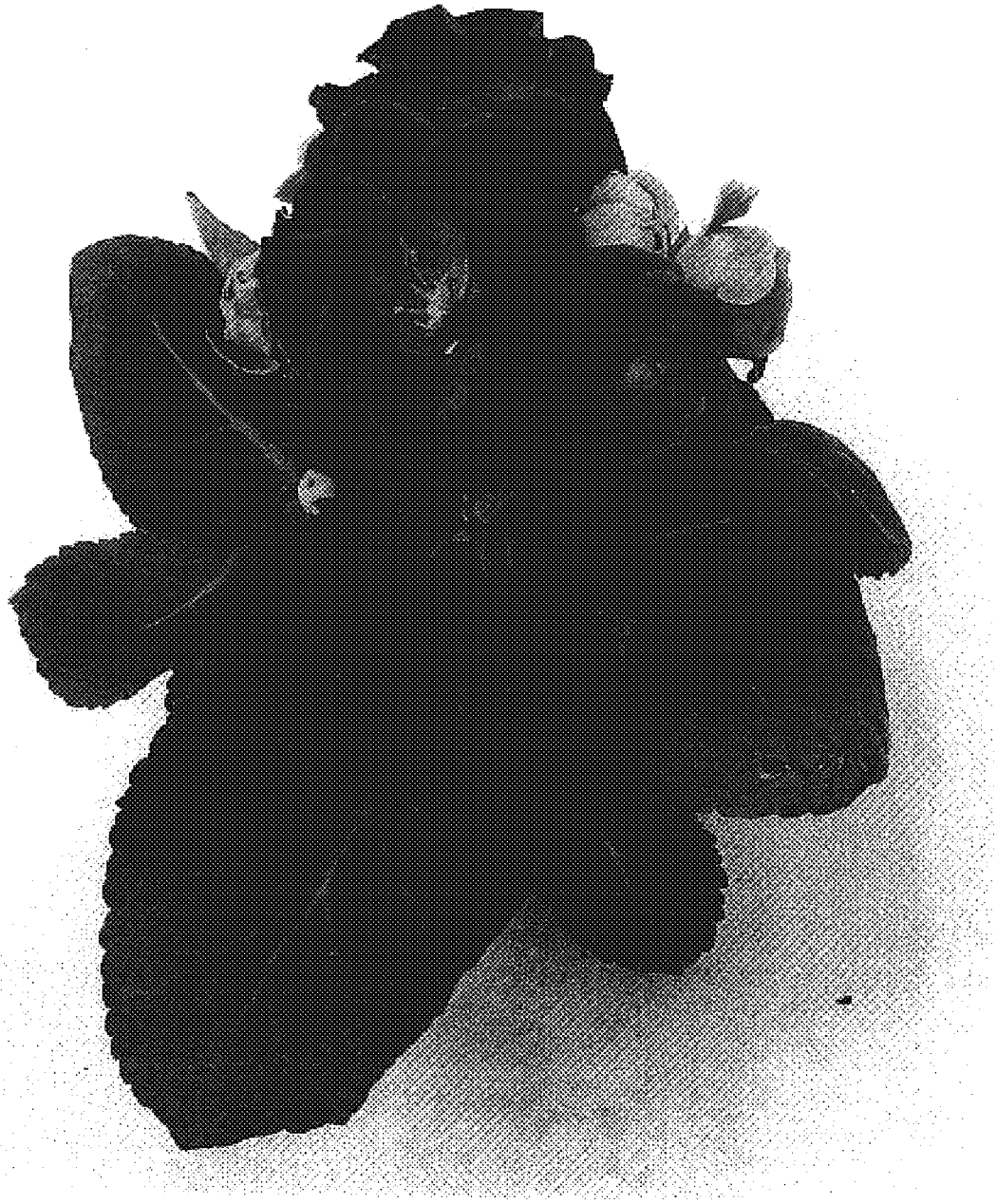

* * * * *